(12) United States Patent
Wollnik et al.

(10) Patent No.: US 9,508,535 B2
(45) Date of Patent: Nov. 29, 2016

(54) ION-MOBILITY SPECTROMETER INCLUDING A DECELERATING ION GATE

(75) Inventors: Hermann Wollnik, Santa Fe, NM (US); Gary A. Eiceman, Las Cruces, NM (US)

(73) Assignee: SHIMADZU CORPORATION, Kyoto-shi (JP)

(*) Notice: Subject to any disclaimer, the term of this patent is extended or adjusted under 35 U.S.C. 154(b) by 0 days.

(21) Appl. No.: 14/384,039

(22) PCT Filed: Mar. 15, 2012

(86) PCT No.: PCT/US2012/029227
§ 371 (c)(1),
(2), (4) Date: Apr. 10, 2015

(87) PCT Pub. No.: WO2013/137883
PCT Pub. Date: Sep. 19, 2013

(65) Prior Publication Data
US 2015/0221489 A1    Aug. 6, 2015

(51) Int. Cl.
*H01J 49/00*    (2006.01)
*G01N 27/62*    (2006.01)
*H01J 49/04*    (2006.01)

(52) U.S. Cl.
CPC ......... *H01J 49/0031* (2013.01); *G01N 27/622* (2013.01); *H01J 49/0422* (2013.01)

(58) Field of Classification Search
USPC ................. 250/290, 286, 281, 282
See application file for complete search history.

(56) References Cited

U.S. PATENT DOCUMENTS

2012/0286156 A1* 11/2012 Park .................. G01N 27/622
                                                250/282

OTHER PUBLICATIONS

International Search Report mailed Jul. 5, 2012 for International Application No. PCT/US2012/029227. (2 Pages).

* cited by examiner

*Primary Examiner* — Kiet T Nguyen
(74) *Attorney, Agent, or Firm* — Morgan, Lewis & Bockius LLP

(57) ABSTRACT

An ion mobility spectrometer having an ion source for generating ions; an ion detector for recording ions, and a number of substantially flat diaphragm electrodes arranged substantially perpendicular to a straight system axis that passes through the apertures in said diaphragms, with the diaphragms being arranged in a series of cells with each cell including an entrances and an exit diaphragm and a short region in between. The exit diaphragm of one cell is identical to the entrance diaphragm of the next cell, and the cells of said ion mobility spectrometer are grouped into three parts: an ion-beam forming region, an ion analyzing region, and a decelerating ion gate.

31 Claims, 4 Drawing Sheets

ION-MOBILITY SPECTROMETER INCLUDING A DECELERATING ION GATE

RELATED APPLICATION

This application is the U.S. national stage application of International (PCT) Patent Application Serial No. PCT/US2012/029227, filed Mar. 15, 2012, the entire disclosure of which is hereby incorporated by reference.

BACKGROUND OF THE INVENTION

1. Technical Field

Aspects of the present invention relate to low-pressure and high-pressure ion mobility spectrometers.

2. Related Art

Ionized large molecules are analyzed in mass spectrometers and in ion mobility spectrometers. In related art, mass spectrometers molecule ions are analyzed by determining their deflections in electromagnetic fields to determine their molecule weight, which is approximately proportional to the volume of a molecule under investigation. Ion mobility spectrometers molecule ions are analyzed by determining their velocities, $v=K*E$, when they are dragged through a buffer gas by an electric field "E" and so their mobilities "K" are approximately proportional to their cross sections.

Ion mobility spectrometers require that the molecule ions to be investigated are entered as short clouds. What are the measured are then the times these clouds need to pass through the length of an ion mobility spectrometer, as is disclosed in G. A. Eiceman and Z. Karpas in "Ion Mobility Spectrometry" 2. ed. Boca Raton, Fla., 2005. What are very important in such ion mobility spectrometers are the used ion gates that form these ion clouds from a continuous ion beam. Such ion gates are for instance disclosed in: A. M. Thyndal, C. F. Powel Proc. Royal Soc. of London 129 (809), (1930) 162 and N. E. Bradbury, R. A. Nielsen, Phys. Rev. 49 (5), (1936) 388. Both of these ion gates consist of harp-like grids placed perpendicular to the incoming ion beam that allow passage of ions only during short time intervals during which the wires of these grids are all at the same potential. At all other times, no ions can pass since different potentials are applied to neighboring wires, in which case the ions are attracted to one of these wires and are so kept from propagating forward in said ion mobility spectrometer.

Related art investigations of molecules have become important in applications for environmental, biological, medical, and pharmacological problems. These related art techniques allow characterization of a molecule not by weight as in a mass spectrometer but by cross section, and thus, by structure since the cross section of a long molecule is certainly bigger when it is stretched out as when it is coiled up. Such characterizations are especially important for the investigation of molecule fragments into which a large molecule breaks up when it absorbs energy, for example, from collisions with buffer gas molecules or atoms.

SUMMARY OF THE INVENTION

An exemplary, non-limiting embodiment of an ion mobility spectrometer, that includes a "decelerating ion gate," comprises at least one ion source, the ion mobility spectrometer, and at least one ion detector, wherein the ion mobility spectrometer comprises an arrangement of substantially flat diaphragms arranged substantially perpendicular to a straight system axis that passes through circular, elliptical or polygonal apertures of the diaphragms. In this ion mobility spectrometer properly chosen potentials are applied to the diaphragms establishing electric fields along the system axis that push ions, that were extracted from at least one ion source, to at least one ion detector, with this direction being called the forward direction. Such an electrode arrangement can be understood as a series of cells with each cell comprising an entrance diaphragm and an exit diaphragm and with the exit diaphragm of one cell being identical to the entrance diaphragm of the downstream neighboring cell.

The electrode arrangement of the ion mobility spectrometer that includes at least one decelerating ion gate is divided into three regions:

- an ion-beam forming region, in which the lateral envelope of a continuous ion beam originating from at least one ion source is shaped by static electric forward fields along the system axis that in most cases differ from one cell to the next
- a decelerating ion gate according to the present invention that comprises at least two cells, i.e. an initial cell A of length $l_A$, and a final cell B of length $l_B$, in which decelerating ion gate time-varied electric forward fields along the system axis divide the continuous ion beam into short ion clouds
- an ion analyzing region in which the ion clouds are moved to at least one ion detector that determines arrival times of the ion clouds and thus the mobilities of the ions contained in these clouds In the ion-beam forming region and in the ion analyzing region the electric forward fields along the system axis are substantially static and have in the $n_{th}$ cell a magnitude $E_n \geq E_H$ with the magnitude of $E_H$ being chosen so that ions of interest of mobility $K_0$ would move forward with a velocity $v_H = K_0 E_H$ of about several meters per second. In the decelerating ion gate, that comprises the cell A and the cell B, the electric forward fields along the system axis are varied over time in three consecutive periods $T_1$, $T_2$, $T_3$ whose durations are chosen so in the chosen fields ions of a range of mobilities $K_0 \pm \Delta K$ can all pass through the decelerating ion gate.

1. During a first time period of duration $T_1$ the ions must move from the ion-beam forming region into cell A of the decelerating ion gate where they are decelerated and thus form a short and dense cloud of ions. This is achieved by choosing the potentials of the entrance and exit diaphragms of cell A so that a low field $E_{A,1} \leq E_H/10$ is established along the system axis in cell A, causing ions of mobilities $K_0 \pm \Delta K$ to be slowed down to a velocity $v_{A,1} = (K_0 \pm \Delta K)E_{A,1}$ when they enter cell A from the last cell of the ion-beam forming region where they moved forward with a velocity $V_H = (K_0 \pm \Delta K)E_H$ in the high electric forward field $\geq E_H$ along the system axis. In order that not even the fastest ions of mobility $K_0 + \Delta K$ have yet reached the exit diaphragm of cell A before the end of $T_1$, it is necessary that the duration of $T_1$ is chosen to be $\leq l_A/[(K_0 \pm \Delta K)E_{A,1}]$.

2. During a second time period of duration $T_2$ the ion cloud is to be pushed out of cell A and into cell B and compressed to a shorter ion cloud. This is achieved by choosing the potentials of the entrance and exit diaphragms of cells A and B so that a high electric forward field $E_{A,2} \geq E_H$ is established along the system axis in cell A and a low electric forward field $E_{B,2} \leq E_H/10$ along the system axis in cell B, causing ions of mobilities $K_0 \pm \Delta K$ to be moved out of cell A with velocities $v_{A,2} = (K_0 \pm \Delta K)E_{A,2}$ and into cell B where they are slowed down to velocities $V_{B,2}=(K_0\pm\Delta K)E_{B,2}$. Here $T_2$ is to be chosen $\geq l_A/[(K_0-\Delta K)E_{A,2}]$ and $\leq l/[(K_0+\Delta K)E_{A,2}]$ so that the ions of lowest mobility $K_0-\Delta K$ have all moved out of cell A and that the ions of highest mobility $K_0+\Delta K$ have all not yet reached the end of cell B at the end of $T_2$.

3. During a third time period of duration $T_3$ the ion cloud is to be pushed out of cell B and into the first cell of the ion analyzing region. This is achieved by choosing the potentials of the entrance and exit diaphragms of cell B so that the electric forward field along the system axis in cell B is $E_{B,3} \geq E_H$, causing ions of mobility $K_0-\Delta K$ to move out of cell B with a velocity $v_{B,2}=(K_0\pm\Delta K)E_{B,2}$ and into the first cell of the "ion analyzing region. Here $T_3$ is to be chosen $\geq l_B/(K_0+\Delta K)E_{B,3})$ so that the ions of lowest mobility $K_0-AK$ have all moved out of cell B at the end of $T_3$. These ions then will enter the first cell of the ion analyzing region where the electric forward field along the system axis is $\geq E_H$ and thus comparable to $E_{B,3}$ so that the velocity of the ions is not changed drastically and the length and shape of the ion cloud stays substantially unchanged.

As soon as the ion cloud has been transferred to the first cell of the ion analyzing region a new first time period of duration $T_1$ can start by establishing again a low electric forward field $E_{A,L} \leq E_H/10$ along the system axis in cell A of at least one decelerating ion gate. Note here also that the transition from one electric field distribution to another at the start of any one of the three time periods is to be short as compared to $T_2$ and/or $T_3$.

At the end of the first time period $T_1$ the length of the ion cloud in cell A is $\Delta l_A \approx T_1 K_0 E_{A,L}$ for ions of mobility $K_0$ as is stated above. However, the upstream end of this ion cloud may not be defined very well since until the last moment of $T_1$ ions are moving into cell A. In order to better define the end of the ion cloud it is advantageous to eliminate the last arriving ions by stopping the ion flow into cell A a short time $\Delta T_1 \ll T_1$ before the start of $T_2$ by changing the potential of at least one of the diaphragms in the ion-beam forming region for this short time, $\Delta T_1$.

In some cases it is advantageous to have mainly ions of low mobilities in the final ion cloud and not the usually abundant ions of high mobilities. To achieve this one can divide the period $T_3$ into two periods $T_{31}$ and $T_{32}$ and extract during the period $T_{31}$ mainly ions of high mobilities out of cell B while ions of low mobilities are left, which after a waiting time $\Delta T_3$ can be extracted during the second period $T_{32}$. Similarly also period $T_2$ can be divided into two periods $T_{21}$ and $T_{22}$ with a waiting time $\Delta T_2$ in between.

In cases in which slightly longer clouds of ions can be tolerated in the ion analyzing region, the electric forward field along the system axis in cell B of the at least one decelerating ion gate can be chosen to be constant and having approximately the same magnitude as $E_{A,H}$. In this case the velocity of ions will not be changed substantially when they leave cell A and enter cell B. Thus, the ion cloud will substantially have the same length in cell B it had, when it was still in cell A.

Since in any space-charge free and conductor free region div(E) must vanish, one finds that ions that are slowed down along the system axis also experience forces that drive them away from the system axis. During the time period $T_1$ such forces are rather strong in the neighborhood of the entrance diaphragm of cell A. As a consequence the lateral ion beam extension increases noticeably when the ions move through cell A. Thus, it is advantageous to increase the aperture of the exit diaphragm of cell A as well as the apertures of all diaphragms in the beam analyzing region in order to let this widened ion beam pass.

In order to keep this beam widening in limits it is advantageous to reduce the ratio between the cross section of the entering ion beam and the area of the aperture in the entrance diaphragm of cell A. The reason is that in this case the ion beam passes only through the middle of this aperture where the fringing field forces that drive ions away from the system axis are smallest.

The best way to reduce the ratio is to reduce the initial lateral width of the ion beam as much as possible before it enters cell A. Such an ion beam of reduced lateral extension can be achieved:

1. by placing at least one explicit lens into the ion acceleration region between the at least one ion source upstream of the ion-beam forming region and/or
2. by decreasing the electric forward field along the system axis in at least one cell of the ion-beam forming region while increasing the field in at least one of the further downstream cells.

Since the ratio between the cross section of the entering ion beam and the area of an aperture is most critical in the aperture of the entrance diaphragm of cell A, one may also increase the aperture in the diaphragm, as long as this increase stays within limits and does not increase the extension of the fringe field in the neighborhood of the diaphragm too much.

Though mechanical grids placed over the apertures of the diaphragm of any cell in the ion mobility spectrometer that includes a decelerating ion gate have the disadvantage that they reduce the ion transmission, there are cases in which it is advantageous to use such grids anyhow. The reason is that at least for a short distance upstream and downstream of a gridded diaphragm all equipotential surfaces are substantially parallel to the grid and thus substantially perpendicular to the system axis. Consequently the electrical forces that act on the ions are mainly parallel to the system axis and the shape of an ion cloud is not distorted in a major way when it passes through the grid.

In the exemplary embodiment of an ion mobility spectrometer that includes a decelerating ion gate such grids are assumed to be placed over the apertures of at least one of three diaphragms:

1. over the aperture in the exit diaphragm of cell A of the decelerating ion gate which is also the entrance diaphragm of cell B. This grid substantially eliminates the otherwise during the period $T_2$ existing fringe field caused by the difference in the high electric field $E_{A,H}$ along the system axis in cell A and the low electric field $E_{B,L}$ along the system axis in cell B.
2. over the aperture in the exit diaphragm of cell B which is also the entrance diaphragm of the first cell of the ion analyzing region. This grid substantially eliminates the otherwise during the period $T_3$ existing fringe field that is caused by the difference in the electric field $E_{B,H}$ along the system axis in cell B and the electric field $\geq E_H$ along the system axis in the first cell of the ion analyzing region.
3. over the aperture in the entrance diaphragm of the first cell of the ion-beam forming region. This grid substantially eliminates the otherwise existing fringe field in the neighborhood of that diaphragm that separates the ion-beam forming region from the ion acceleration region, i.e. the region in which the ions are extracted from the at least one ion source and pushed into the ion-beam forming region. Such a grid also protects the ion-beam forming region from possible high-voltage discharges to the at least one ion source.

Since fringing fields may be detrimental between neighboring cells throughout the mobility spectrometer that includes a decelerating ion gate it is in many cases also advantageous to modify the fringing fields by placing an extra tubular electrode between the entrance and exit diaphragms of a cell under investigation. Herein the potential of this tubular electrode is advantageously chosen to be in the range between the potentials of the entrance and exit diaphragms of a respective cell.

BRIEF DESCRIPTION OF THE DRAWINGS

The above and/or other aspects and features will become apparent and more readily appreciated from the following description of the exemplary embodiments, taken in conjunction with the accompanying drawings, in which.

DETAILED DESCRIPTION OF THE INVENTION

Figure 1:
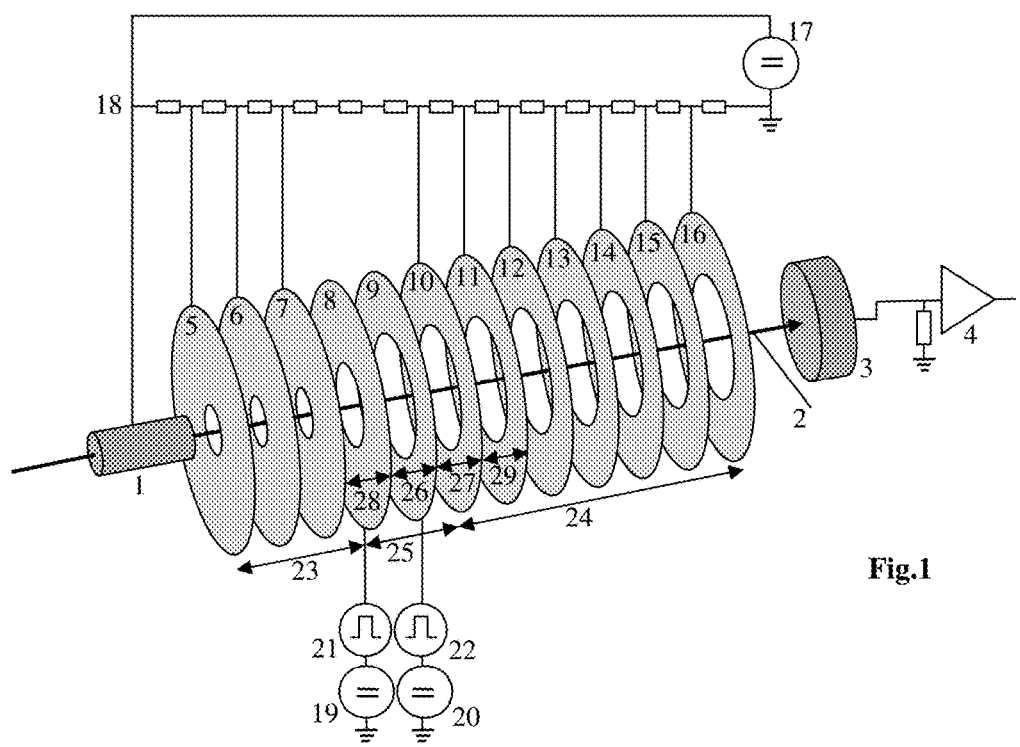
FIG. 1 is a schematic view of the mechanical design of a first exemplary, non-limiting embodiment of an ion mobility spectrometer that includes at least one decelerating ion gate built from a series of diaphragms placed at different electric potentials.

Exemplary embodiments will be described in greater detail with reference to the accompanying drawings. In the following description, the same drawing reference numerals are used for the same elements in all drawings. The matters defined in the description such as a detailed construction and arrangement of elements are only those provided to assist in a comprehensive understanding of the invention. Thus, it is apparent that the present invention can be carried out without being limited to those defined matters. Also, well-known functions or constructions are not described in detail since they would obscure the invention in unnecessary detail.

FIG. 1 is a schematic view of the mechanical arrangement of an exemplary, non-limiting embodiment of a mobility spectrometer that comprises a decelerating ion gate. In total ions are moved from an ion source 1 through the ion mobility spectrometer to an ion detector 3 from where collected ion charges are conducted to an amplifier 4. The electric fields throughout the mobility spectrometer are formed by potentials applied to diaphragms 5, 6, 7, 8, 9, 10, 11, 12, 13, 14, 15, 16 shown in FIG. 1. These potentials are provided from a static voltage supply 17 and a resistive voltage divider 18 as well as by two static voltage generators 19 and 20 and by two pulsed voltage generators 21 and 22.

The ion mobility spectrometer shown in FIG. 1 can be understood as being divided into three parts:

1. An ion beam-forming region 23, that consists of three cells formed between diaphragms 5, 6 and 6, 7 and 7, 8 that all are shown to have circular, elliptical or polygonal apertures of substantially equal areas $\approx \sigma_0$. Through this ion beam-forming region 23 a continuous ion beam is pushed by electric forward fields $E_{5,6} \approx E_{6,7} \approx E_{7,8} \geq E_H$ along the system axis 2 formed by the potentials of the diaphragms 5, 6, 7, and 8. Here the magnitude of $E_H$ is to be chosen so that ions of interest of mobility $K_0$ move forward with a velocity $V_H \approx K_0 E_H$ of several meters per second. Often used is here an arrangement in which $E_{6,7} > E_{5,6}$ and/or $E_{7,8} > E_{6,7}$ since this causes a reduction of the lateral width of the passing ion beam.

2. An ion analyzing region 24, that consists of the six cells formed between the diaphragms 10, 11, 12, 13, 14, 15, and 16 that all have circular, elliptical or polygonal apertures of substantially equal areas which, however, are noticeably larger than those in the diaphragms 5, 6, 7, and 8 of the ion-beam forming region 23 and thus allow a widened ion beam to pass. Through this ion analyzing region 24 clouds of ions are moved by electric forward fields $E_{10,11} \approx E_{11,12} \approx E_{12,13} \approx E_{13,14} \approx E_{14,15} \approx E_{15,16} \geq E_H$ formed by the potentials of said diaphragms 10, 11, 12, 13, 14, 15, and 16.

3. A decelerating ion gate 25 in which the continuous ion beam injected from the ion-beam forming region 23 is split into short ion clouds of high ion density. This ion gate 25 comprises a cell A 26 of length $l_A$ formed between the diaphragms 8,9 and a cell B 27 of length $l_B$ formed between the diaphragms 9,10. The apertures in the entrance and exit diaphragms 9 and 10 of cell B here are shown in FIG. 1 to be substantially equal to the large apertures in the diaphragms 10, 11, 12, 13, 14, 15, and 16 of the ion analyzing region, while the aperture in the entrance diaphragm 8 of cell A 26 is shown in FIG. 1 to be equal or only slightly larger than the apertures in the diaphragms 5, 6, and 7 of the ion-beam forming region 23. The potentials of all diaphragms are shown to be fixed by corresponding taps of the potential divider 18 while the potentials of the diaphragms 8 and 9 are shown to be determined by the sum of static voltage generators 19 and 20 and pulse generators 21 and 22 the output of which may vary during three time periods $T_1$, $T_2$, and $T_3$. The durations of these time periods are chosen so that with proper potentials applied to the diaphragms 8, 9, and 10 during the time periods $T_1$, $T_2$, and $T_3$ ions of mobilities $K_0 \pm \Delta K$ are passed through said decelerating ion gate 25 and compressed to short ion clouds.

3.1 During a first period $T_1$, which in most cases lasts for many milliseconds, these potentials are to be chosen so that they cause the electric forward field along the system axis in cell A 26 of length $l_A$ to be $E_{A,1} \leq E_H/10$, an electric field that it is much smaller than said static electric forward field $E_{7,8} \geq E_H$ along the system axis in the last cell 28 between the diaphragms 7 and 8 of the ion-beam forming region 23. Consequently all ions move out of this cell 28 with high velocities and are slowed down when they enter cell A 26 thus, forming high density ion clouds in cell A, wherein such ion clouds are shorter for ions of low mobilities than for ions of high mobilities. The duration of $T_1$ here should be chosen to be $\leq l_A/[(K_0+\Delta K)E_{A,1}]$ so that at the end of $T_1$ even the ions of the highest mobilities $(K_0+\Delta K)$ form an ion cloud of length $\leq l_A$ and thus are contained in cell A 26. At the end of the period $T_1$, however, some of the ions of mobilities $\geq (K_0+\Delta K)$ have already passed through the full length $l_A$ of cell A 26 and thus are lost.

3.2 During a second period $T_2$ that in most cases lasts for $\approx 1$ ms, these voltages are chosen so that they cause the electric field along the system axis in cell A 26 of length $l_A$ to be $E_{A,2} \geq E_H$ and in cell B 27 of length $l_B$ to be $E_{B,2} \leq E_H/10$. Consequently all ions move out of cell A with high velocities and are slowed down when they enter cell B thus forming even denser ion clouds of lengths $\Delta l_B \approx \Delta l_A(E_{B,2}/E_{A,1})$ in cell B if they had lengths $\Delta L_A \leq l_A$ in cell A.

The duration of $T_2$ here should be chosen to be $\geq l_A/[(K_0-\Delta K)E_{A,2}]$ and $\leq l_B/[(K_0+\Delta K)E_{B,2}]$ so that at the end of $T_2$ even the ions of lowest mobilities $(K_0-\Delta K)$ are transferred out of cell A 26 and into cell B 27, while ions of highest mobilities $(K_0+\Delta K)$ have not yet reached the end of cell B 27. Some of the ions of mobilities $\geq (K_0+\Delta K)$, however, have already passed through the full length $l_B$ of cell B and thus are lost at the end of $T_2$, while some of the ions of mobilities $\leq (K_0-\Delta K)$ have not yet left cell A and thus are lost as well.

3.3 During a third period $T_3$, that also lasts for $\approx 1$ ms in cell B these voltages must be chosen so that they cause the electric field along the system axis in cell B 27 of length $l_B$ to be $E_{B,3} \geq E_H$ while the electric field along the system axis in the first cell 29 between the diaphragms 10 and 11 of the ion analyzing region 24, is about equal to said static electric forward field $E_{10,11} \geq E_H$ along the system axis. Consequently all ions move with about equal velocities from cell 27 into cell 29 and thus form there ion clouds of length $\Delta l_{10,11} \approx \Delta l_B(E_{10,11}/E_{B,3})$ if they had lengths $\Delta l_B$ in cell B. However, since $E_{B,3}$ and $E_{10,11}$ are not drastically different, the lengths, shapes and densities of the ion clouds stay more or less unchanged relative to what they were in cell B 27.

The duration of $T_3$ here is chosen to be $\geq l_B/[(K_0-\Delta K)E_{B,3}]$ so that at the end of $T_3$ even the ions of lowest mobilities $(K_0+\Delta K)$ are transferred out of cell B 27 and into cell 29 of the ion analyzing region 24, while some of the ions of mobilities $\leq (K_0-\Delta K)$ have not yet left cell B and thus are lost. As soon as the ion cloud has been transferred to the first cell 29 of the ion analyzing region a new time period $T_1$ can start by establishing again a low electric field $E_{A,1} \leq E_H/10$ along the system axis in cell A 26.

Since in any space-charge free and conductor free region div(E) must vanish, ions that are slowed down along said system axis also experience forces that drive them away from this axis. During the relatively long time period $T_1$ such forces are rather strong for a short distance downstream of diaphragm 8, the entrance diaphragms of cell A 26. As a consequence the lateral ion beam extension increases noticeably when it enters cell A 26 in which case it is advantageous to increase the aperture of the diaphragm 9 of cell A 26 as well as the apertures of the diaphragms 10, 11, 12, 13, 14, 15, and 16 in the beam analyzing region in order to let this widened ion beam pass.

In order to keep said beam widening in limits, it is advantageous to reduce the ratio between the cross section of the ion beam and the area of the aperture of the diaphragm through which the ion beam passes, since in this case the ion beam passes only through the middle of this aperture where the fringing field forces that drive ions away from said system axis are smallest. Especially important is for the ion beam to pass through the apertures of said diaphragms 8 and 9 the entrance and exit diaphragms of cell A.

The best way to reduce this ratio is to reduce the initial lateral width of the ion beam as much as possible before it reaches these diaphragms. Such ion beams of reduced lateral extensions can be achieved:

1. by placing at least one explicit lens (not shown in FIGS. 1, 2) into the ion acceleration region between the ion source 1 upstream of the ion-beam forming region 23 and/or
2. by decreasing the electric forward field along said system axis in at least one cell of said ion-beam forming region 23 while increasing said electric forward field in at least one of the further downstream cells.
3. by increasing the aperture in the entrance diaphragm 8 of cell A slightly as long as this increase stays within limits and does not increase the extension of the fringe field in the neighborhood of diaphragm 8 too much.

Though mechanical grids placed over the apertures of the diaphragm of any cell in the ion mobility spectrometer that includes a decelerating ion gate have the disadvantage that they reduce the ion transmission, there are cases in which it is advantageous to use such grids. The reason is that at least for a short distance upstream and downstream of a gridded diaphragm all equipotential surfaces are substantially parallel to said grid and thus substantially perpendicular to the system axis. Consequently the electrical forces that act on the ions are substantially parallel to the system axis and the length and shape of an ion cloud is not distorted substantially when it passes through said grid.

Figure 2:
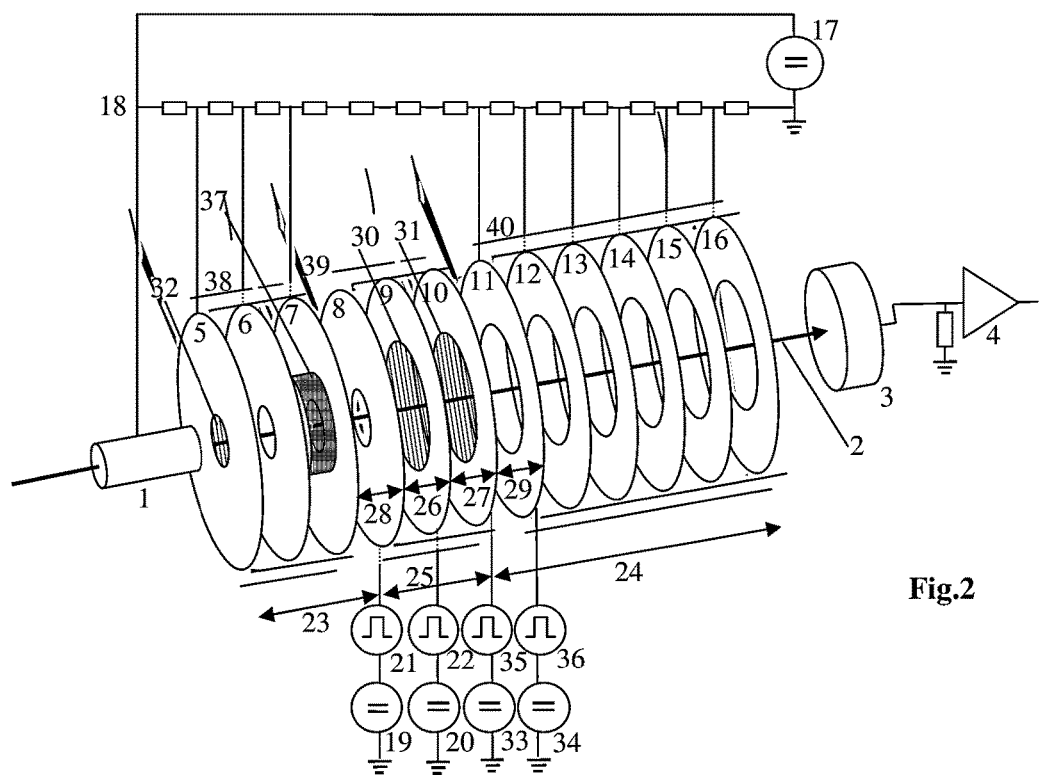
FIG. 2 is identical to FIG. 1 except that in this embodiment grids are placed over the apertures of the diaphragms 5, 8, and 9, that two additional static voltage generators 33, 34 and two additional pulse generators 35,36 are installed and that a conductive tube is placed around the ion mobility spectrometer with this tube being divided into several sections.

FIG. 2 is very similar to FIG. 1 and also shows an exemplary embodiment of an ion mobility spectrometer that includes a decelerating ion gate. The difference is that in FIG. 2 mechanical grids 30, 31, and 32 are assumed to be placed over the apertures of at least one of three diaphragms:

1. A grid 30 placed over the aperture in diaphragm 9 substantially eliminates the otherwise during said period $T_2$ existing fringe field caused by the difference in the high electric field $E_{A,2} \geq E_H$ along the system axis in cell A 26 and the low electric field $E_{B,2} \leq E_H/10$ along the system axis in cell B 27.
2. A grid 31 placed over the aperture in diaphragm 10 substantially eliminates the otherwise during said period $T_3$ existing fringe field caused by the difference in the high electric field $E_{B,3} \geq E_H$ along the system axis in cell B 27 and the about equally large electric field $\geq E_H$ along the system axis in cell 29, the first cell of the ion analyzing region 24.
3. A grid 32 placed over the aperture in diaphragm 5 substantially eliminates the otherwise existing fringe field caused by the difference in the ion-beam forming region 23 and in the ion acceleration region in which the ions are extracted from the ion source 1 and pushed into the ion-beam forming region 23. Such a grid also widely protects the ion-beam forming region 23 from possible high-voltage discharges to the ion source 1.

In order to allow more flexibility in steering the electric fields in said decelerating ion gate, it may be advantageous to provide additional DC and pulsed power supplies 33,34 and 35,36 that can vary the potential of diaphragm 10.

Analogously and also advantageously one could also supply such steering voltages (not shown) to other diaphragms upstream or downstream of the decelerating ion gate.

Since fringe fields may be detrimental between neighboring cells throughout a mobility spectrometer that includes a decelerating ion gate it is in many cases also advantageous to modify said fringing fields by placing extra tubular electrodes between the entrance and exit diaphragms of any cell under investigation. Such a tubular electrode 37 is shown between the diaphragms 6 and 7. Herein the potentials of such tubular electrodes are advantageously chosen to be within the range between the potentials of the corresponding entrance and exit diaphragms.

In order to protect the ion mobility spectrometer, that includes an ion decelerating ion gate, from the influence of outside electric fields it is advantageous to place shielding tubes 38, 39, 40 around sections of said ion mobility spectrometer. Applying different potentials to said shielding tubes 38, 39, and 40 allows to influence the potential distribution in the cell around which the shielding tubes are placed.

Though the decelerating ion gate provides narrow ion clouds of high intensity, it may be useful to further reduce their length by placing a Bradbury-Nielson Gate (not shown) within or downstream of the decelerating ion gate. Such a Bradbury-Nielson Gate could for instance replace the grid 30 placed over the aperture of the exit diaphragm of the cell B 27, the diaphragm 10.

In FIGS. 3, 4 examples are shown how the potentials of the different diaphragms could be chosen to form the above described electric fields during said time periods $T_1$, $T_2$, and $T_3$. Naming the potential of a diaphragm N as $U_N$ one may choose the potentials of diaphragms N in the ion-beam forming region as well as in the ion analyzing region as static potentials, wherein the potentials $U_i$ is substantially more ion repelling than the potentials $U_{i+1}$ with i=5, 6, 7 and i=11, 12, 13, 14, 15. The potentials $U_8$, $U_9$, $U_{10}$, however, are varied to achieve the required electric fields during said time periods $T_1$, $T_2$, $T_3$ in cell A and in cell B by activating said static voltage generators 19, 20, 33, 34 as well as said pulsed voltage generators 21, 22, 35, 36.

FIG. 3 illustrates one example how to choose potentials for the diaphragms 8 and 9 as $U_8=U_7-V_1$ and $U_{10}=U_8-V_2=U_{11}+V_3$ with $V_1$, $V_2$ and $V_3$ being ion repelling voltages determined by the resistive voltage divider 18 while $V_9$ is varied so, that $V_9=V_8$ during the time periods $T_1$ and $T_3$ and $V_9=V_{10}$ during the time period $T_2$.

Figure 3A:
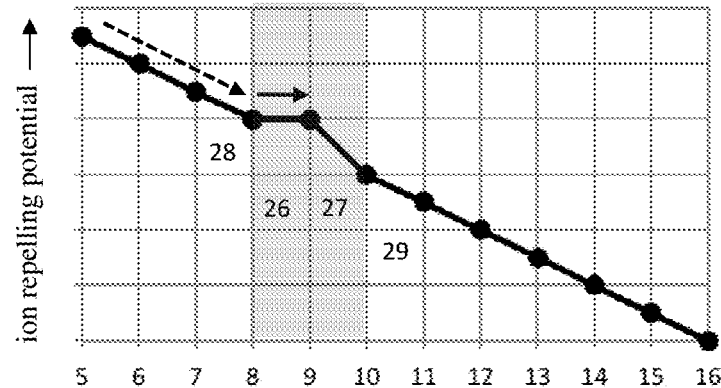
FIGS. 3a-3c are a schematic view of the potentials of the diaphragms of the ion-mobility spectrometer that includes at least one decelerating ion gate during said different periods $T_1$, $T_2$, $T_3$ for an exemplary, non-limiting way to change the potential of a single diaphragm in order to achieve the necessary field strengths throughout the ion mobility spectrometer wherein the potentials of all diaphragms are static except one.
Figure 3B:
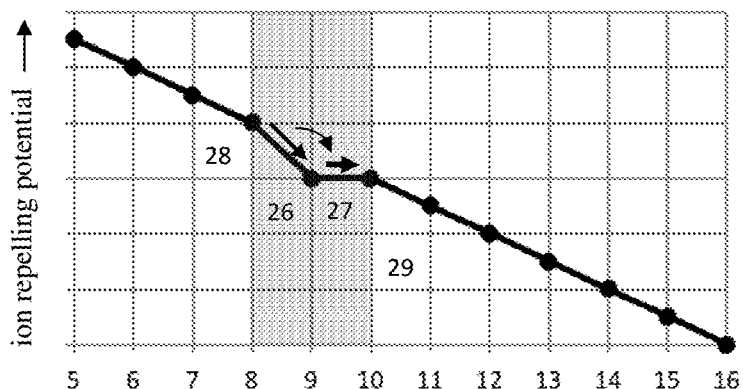

In FIG. 3a the potential distribution is shown during the time period $T_1$, wherein the continuous ion flux in the ion-beam forming region between the diaphragms 5 and 8 is indicated as a dashed arrow and the compressed ion cloud at the end of the time period $T_1$ in cell A 26 between the diaphragms 8 and 9 as a short arrow, In FIG. 3b the potential distribution is shown during the time period $T_2$, wherein the transfer of the ion cloud from cell A 26 between the diaphragms 8 and 9 into cell B 27 between the diaphragms 9 and 10 is indicated as a curved arrow and two solid arrows indicate that the ion cloud in cell B 27 is shorter than it was in cell A 26.

Figure 3C:
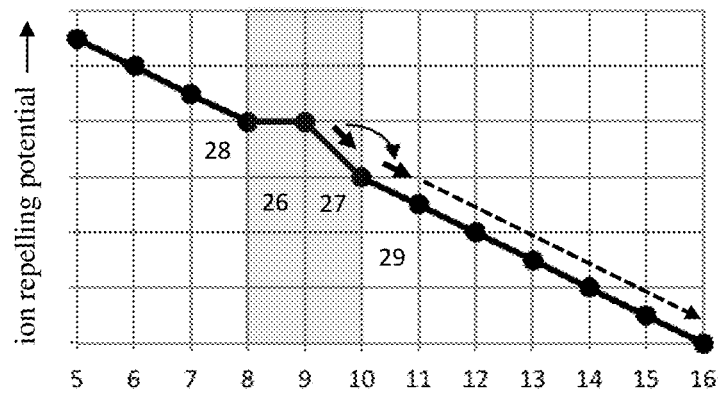

In FIG. 3c the potential distribution is shown during the time period $T_3$, wherein the transfer of the ion cloud from cell B 27 between the diaphragms 8 and 9 into the first cell of the ion analyzing region 29 between the diaphragms 10 and 11 is indicated as a curved arrow and two solid arrows indicate that the ion clouds in cell B 27 and the first cell of the ion analyzing region 29 are approximately equal in length. By a dashed arrow also the path is indicated along which the ion clouds of different mobilities move through the ion analyzing region between the diaphragms 10 and 16.

The same field distribution could be achieved by choosing $U_{10}=U_{11}+V_3$ as a fixed potential and by establishing $U_8=U_9=U_{10}$ during the time period $T_1$, $U_8=U_{10}+\Delta V_1$ and $U_9=U_{10}$ during the time period $T_2$, and $U_8=U_{10}$ and $U_9=U_{10}+\Delta V_1$ during the time period $T_3$.

In both mentioned examples the ions are still streaming into cell A during the time period $T_2$, when the accumulated ion cloud moves from cell A into cell B.

Consequently the ion cloud that is extracted from cell A has a small tail which, however, in most cases is negligible. However, this tail is eliminated when during the last milliseconds or so of the time period $T_1$ the influx of ions into cell A is prohibited by raising the potential of one of the last diaphragms in the ion-beam forming region 23 as has been proposed already above.

Besides the listed examples of how to properly choose the potentials of the diaphragms 8, 9, 10 in the decelerating ion gate there are several alternate ways that all would achieve similar electric fields along the system axis in cell A and in cell B during said times $T_1$, $T_2$, and $T_3$ and thus similar ion clouds.

Figure 4A:
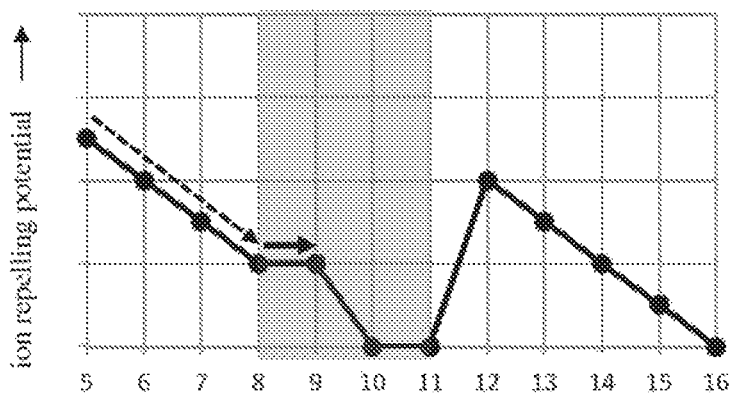
FIGS. 4a-4c are a schematic view of the potentials of the diaphragms of the ion-mobility spectrometer that includes at least one decelerating ion gate during said different periods $T_1$, $T_2$, and $T_3$ for an exemplary, non-limiting way to change the potentials of two diaphragms in order to achieve the necessary field strengths throughout the ion mobility spectrometer as shown in FIG. 3, wherein, however, the range of the overall potentials is reduced, which requires that during the time $T_3$ a voltage V00 is added to the potentials of at least three diaphragms.
Figure 4B:
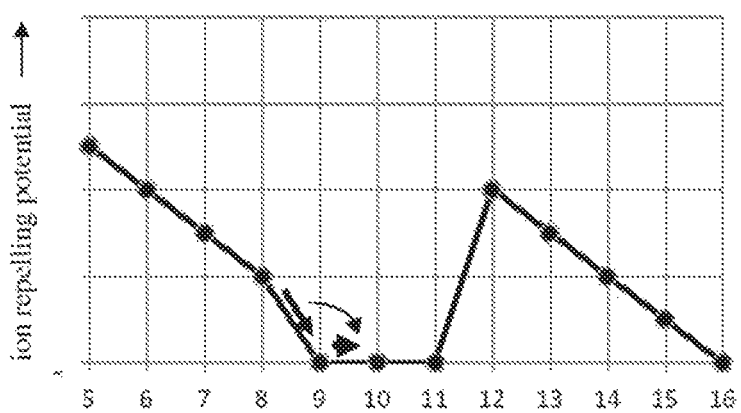
Figure 4C:
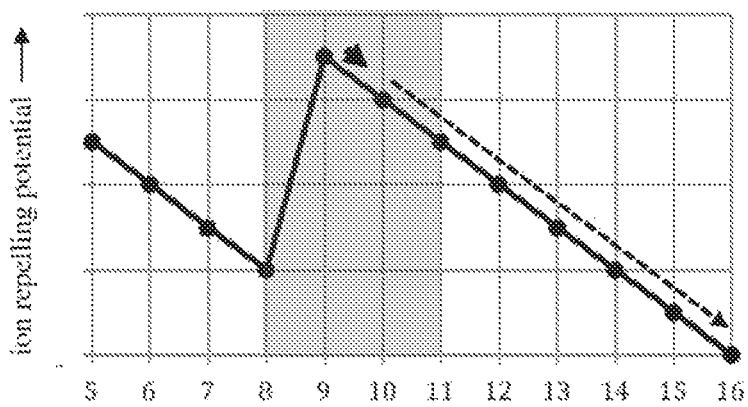

The voltage difference between the diaphragms 5 and 16 is large and thus there is always the danger of high voltage discharges. Thus it usually is usually rewarding to reduce this potential difference. One way is to permanently subtract, as is illustrated in FIG. 4, from the potentials of the diaphragms 5, 6, 7, 8, 9, 10, and 11 (see FIG. 3) a voltage $V_{00}$ and to add this voltage $V_{00}$ again to the diaphragms 9, 10, 11 during the time period $T_3$. The resultant potential distribution is shown in FIGS. 4a, 4b, and 4c for the three time periods $T_1$, $T_2$, and $T_3$. This procedure requires, however, that a grid is placed over the aperture in the diaphragm 9. In case there is no such grid it is necessary to add this voltage $V_{00}$ additionally to diaphragm 8 during the time period $T_3$.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ion mobility spectrometer comprising:
   an ion source for generating ions;
   an ion detector for recording ions, and
   a number of substantially flat diaphragm electrodes arranged substantially perpendicular to a straight system axis that passes through apertures in said diaphragms, with the diaphragms being arranged in a series of cells with each cell comprising an entrance diaphragm and an exit diaphragm and a short region in between, wherein the exit diaphragm of one cell is identical to the entrance diaphragm of the next cell, and wherein said cells of said ion mobility spectrometer are grouped into three parts:
   an ion-beam forming region comprising at least one of said cells with its diaphragms having circular, elliptical or polygonal apertures of substantially equal areas $\sigma_0$;
   an ion analyzing region comprising at least one of said cells with its diaphragms having circular, elliptical or polygonal apertures whose areas are substantially equal but larger than $\sigma_0$; and
   a decelerating ion gate placed downstream of said ion-beam forming region and upstream of said ion analyzing region wherein said decelerating ion gate comprises at least two cells, an initial cell A of length $l_A$ and a final cell B of length $l_B$, wherein an entrance diaphragm of said cell A is equal to or greater than a last diaphragm of the ion-beam forming region having an aperture of area $\sigma_0$, while an exit diaphragm of said cell B is identical to a first diaphragm of the ion analyzing region having an aperture whose area is substantially larger than $\sigma_0$, while diaphragms between the entrance diaphragm of said cell A and the exit diaphragm of said cell B have apertures whose areas are in between the area of the aperture of the entrance diaphragm of said cell A and the area of the aperture of the exit diaphragm of said cell B.

2. An ion mobility spectrometer according to claim 1, wherein to the diaphragms in said ion-beam forming region and in said ion analyzing region, substantially static potentials are applied creating electric fields, that move ions in a forward direction from said ion source to said ion detector with the magnitude of these electric forward fields being $\geq E_H$ along the system axis, with $E_H$ having a magnitude such that in this field ions of mobility $K_0$ would move forward with a velocity $v_H = K_0 E_H$ of about several meters per second, and wherein during three different time periods $T_1$, $T_2$, and $T_3$, different potentials are applied to the diaphragms in said cells A and B of said decelerating ion gate, wherein during a first time period $T_1$ the potentials of the entrance and exit diaphragms of said cell A in said decelerating ion gate are such that a low electric forward field along the system axis in cell A, $E_{A,1}$, where $E_{A,1} \leq E_H/10$, is established, while in the last cell of said ion-beam forming region the electric forward field is $\geq E_H$ along the system axis, which causes the incoming ions to move into cell A, where they are slowed down and form a dense ion cloud, and wherein further during a second time period $T_2$ the potentials of the entrance and exit diaphragms in said cells A and B in said decelerating ion gate are such that a low electric forward field along the system axis in cell B, $E_{B,2}$ where $E_{B,2} \leq E_H/10$ exists, while a high electric forward field along the system axis in cell A, $E_{A,2}$, where $E_{A,2} \geq E_H$ exists, so that the ion cloud moves out of cell A and into cell B where the ions are slowed down again and form a new ion cloud that is shorter and thus denser than it was in cell A at the beginning of said time period $T_2$, and wherein during a third time period $T_3$ the potentials of the entrance and exit diaphragms in said cell B in said decelerating ion gate are chosen so that a high electric forward field along the system axis in cell B, $E_{B,3}$, where $E_{B,3} \geq E_H$ exists whose magnitude is substantially equal to the electric forward field along the system axis in the first cell of the ion analyzing region so that the ion cloud moves out of cell B and into said first cell of the ion analyzing region without changing the velocities of the ions substantially in which case the ion cloud keeps approximately the length and shape it had in cell B at the beginning of said time period $T_3$.

3. An ion mobility spectrometer according to claim 2, wherein the durations of said three time periods $T_1$, $T_2$, and $T_3$ are chosen so that ions of interest of a range of mobilities $K_0 \pm \Delta K$ where $\Delta K$ is a small change in $K_0$ can all pass through said decelerating ion gate, wherein the duration of said time period $T_1$ is chosen to be $\leq l_A/[(K_0+\Delta K)E_{A,1}]$ with $E_{A,1} \leq E_H/10$, so that at the end of said time period $T_1$ even the fastest ions of interest of mobility $K_0+\Delta K$, have not yet reached the end of said cell A of length $l_A$, and wherein the duration of said time period $T_2$ is chosen to be $\geq l_A/[(K_0-\Delta K)E_{A,2}]$ and $\leq l_B/[(K_0+\Delta K)E_{B,2}]$ with $E_{A,2} \geq E_H$ and $E_{B,2} \leq E_H/10$, so that at the end of said time period $T_2$ even the slowest ions of interest of mobility $(K_0-\Delta K)$, have moved out of cell A of length $l_A$ while the fastest ions of interest of mobility $(K_0+\Delta K)$, have not yet passed through the full length $l_B$ of cell B, and wherein the time period $T_3$ is chosen to be $\geq l_B/[(K_0-\Delta K)E_{B,3})$ with $E_{B,3} \geq E_H$, so that at the end of said time period $T_3$ even the slowest ions of interest of mobility $K_0-\Delta K$, have moved out of cell B.

4. An ion mobility spectrometer according to claim 2, wherein a short time prior to the end of said time period $T_1$ the potential of one of the last diaphragms in the ion-beam formation region is made more ion repellent for a short period $\Delta T_1 \ll T_1$ where $\Delta T_1$ is a small change in $T_1$ so that the flux of ions into cell A of said decelerating ion gate is stopped shortly before the end of the time period $T_1$.

5. An ion mobility spectrometer according to claim 2, wherein constant potentials are applied to the entrance and exit diaphragms in said "cell B", establishing a static electric forward field $> E_H$ along said system axis in cell B.

6. An ion mobility spectrometer according to claim 2, wherein said time period $T_3$ is divided into two time periods $T_{31}$ and $T_{32}$ separated by a short time of duration $\Delta T_3$, where $\Delta T_3$ is some small change in $T_3$ and/or wherein said time period $T_2$ is divided into two time periods $T_{21}$ and $T_{22}$ separated by a waiting time of duration $\Delta T_2$, where $\Delta T_2$ is a small change in $T_2$ so that two ion clouds are formed the second of which contains mainly ions of low mobilities.

7. An ion mobility spectrometer according to claim 6, wherein a Bradbury-Nielson Gate, is placed into the aperture of the exit diaphragms of cell B or into the aperture of at least one of the diaphragms of the ion analyzing region, wherein to said Bradbury-Nielson Gate ion flux barring voltages are applied during the time period during which ions of said cloud of ions of high mobilities reach said Bradbury-Nielson Gate.

8. An ion mobility spectrometer according to claim 6, wherein at least in one of the cells of the ion analyzing region, an electric field is established, that during the time period, during which ions of said cloud of ions of high mobilities reach said cell, has a substantial field component perpendicular to said system axis, wherein such a field component is achieved by dividing at least one of the diaphragms of said at least one cell in an upper and a lower half diaphragm or by adding within said cell explicit extra electrodes similar to a small parallel plate condenser to which electrodes or half diaphragms voltage pulses are applied during said time period, during which ions of said cloud of ions of high mobilities reach said cell so that during a short time period electric field components perpendicular to the system axis exist.

9. An ion mobility spectrometer according to claim 2 wherein the static electric forward field along the system axis in one cell of said ion-beam forming region is substantially lower than the static electric forward field along the system axis in at least one of the next cells.

10. An ion mobility spectrometer according to claim 9 wherein the electric forward fields in consecutive cells are chosen so that they together approximate a field that would be formed by an ion attracting downstream positioned point charge placed at some position on said system axis.

11. An ion mobility spectrometer according to claim 2, wherein static potentials $U_A$ and $U_B$ are applied to the entrance diaphragm of cell A, and to the exit diaphragm of cell B, respectively, with $U_A$ being much more ion repelling than $U_B$ that a field $\geq E_H$ would be formed if all diaphragms between the entrance diaphragm of cell A and the exit diaphragm of cell B are removed, while the potential of the entrance diaphragm of cell B which is also the exit diaphragm of cell A, is varied so that a low electric forward fields $\leq E_H/10$ exists between the entrance of diaphragm of cell B and the exit diaphragm of cell A during the time periods $T_1$ and $T_3$ and that during the time period $T_2$ a low electric forward fields $\leq E_H/10$ exists between the entrance and exit diaphragms of cell B.

12. An ion mobility spectrometer according to claim 11, wherein during said time periods $T_1$ and $T_2$ an ion repellent voltage $V_{00}$ is subtracted from the potentials of the first two diaphragms of the ion analyzing region and all other diaphragms upstream in the decelerating ion gate and the ion-beam forming region, and wherein during the time period $T_3$ said ion repellent voltage $V_{00}$ is again added to the potentials of the first two diaphragms of the ion analyzing region, as well as to the entrance diaphragm of cell B in case a grid is placed over the aperture of this diaphragm and additionally also to the potential of the entrance diaphragm of cell A in case that said grid is omitted.

13. An ion mobility spectrometer according to claim 2, wherein during said time periods $T_1$, $T_2$, and $T_3$ only the potentials of the entrance and exit diaphragms of cell A, $U_{A1}$ and $U_{A2}$, respectively, are varied, while a static potential $U_B$ is applied to the first diaphragm of said ion analyzing region, which is also the exit diaphragm of said cell B,
wherein $U_{A1} \approx U_{A2} \approx U_B$ during said time period $T_1$ and
wherein $U_{A2} \approx U_B$ and $U_{A1} = U_B + V_1$ during said time period $T_2$ with $V_1$ being an ion repellent voltage, and
wherein $U_{A1} \approx U_B$ and $U_{A2} = U_B + V_2$ during said time period $T_3$ with $V_2$ being an ion repellent voltage.

14. An ion mobility spectrometer according to claim 13, wherein during said time periods $T_1$ and $T_2$ an ion repellent voltage $V_{00}$ is subtracted from the potentials of the first two diaphragms of the ion analyzing region and all other diaphragms upstream in the decelerating ion gate and the ion-beam forming region, and wherein during the time period $T_3$ said ion repellent voltage $V_{00}$ is again added to the potentials of the first two diaphragms of the ion analyzing region, as well as to the potential of the entrance diaphragm of cell B in case a grid is placed over the aperture of this diaphragm and additionally also to the potential of the entrance diaphragm of cell A in case that said grid is omitted.

15. An ion mobility spectrometer according to claim 1, wherein said decelerating ion gate, comprises three main diaphragms that form said cell A and said cell B, the entrance diaphragm of cell A, the exit diaphragm of cell B, and the exit diaphragm of cell and which is identical to the entrance diaphragm of cell B, wherein both cells A and B comprise several subcells and wherein to the diaphragms of these subcells potentials are supplied that cause the electric forward fields in said subcells to be substantially equal to the overall fields in cell A and in cell B, respectively.

16. An ion mobility spectrometer according to claim 15, wherein the potentials of at least one of the diaphragms of said cell A and/or said cell B are not switched instantly at the start of said time periods $T_1$ and/or $T_2$ and/or $T_3$ to their new values but are rather varied in such a manner that the resultant electric forward fields take up intermediate values for a short period of $\approx 100$ µs before they are switched to their final values.

17. An ion mobility spectrometer according to claim 1, wherein conductive grids cover the apertures in the exit diaphragm of said cell A and/or of said cell B in said decelerating ion gate and/or in at least one of the diaphragms in the ion-beam forming region and/or in at least one of the diaphragms in the ion analyzing region, wherein these grids are etched grids, woven grids, or harp grids that comprise only of a number of parallel wires.

18. An ion mobility spectrometer according to claim 17, wherein at least one of said grids is replaced by a Bradbury-Nielson Gate.

19. An ion mobility spectrometer according to claim 1 wherein between the two diaphragms of at least one of said cells at least one conductive tubular electrode of substantially circular or polygonal cross section is placed in such a way that the axis of said tubular electrode substantially coincides with said system axis, wherein to said tubular electrode a potential is applied that has a value that is either substantially between the potentials of the two diaphragms that limit the cell under consideration or that moderately exceeds any one of these potentials.

20. An ion mobility spectrometer according to claim 19, wherein said tube is either a straight tube, a conical tube, or a trumpet-like shaped tube.

21. An ion mobility spectrometer according to claim 19, wherein said potential applied to said tubular electrode varies over time.

22. An ion mobility spectrometer according to claim 19, wherein said tubular electrode is formed from material of high resistivity or is formed from insulating material covered by a layer of material of high resistivity so that one can pass a small current through this inner surface of said tubular electrode.

23. An ion mobility spectrometer according to claim 1 in which an electric lens is placed between said ion source and said beam forming region.

24. An ion mobility spectrometer according to claim 23 wherein said electric lens is formed as a Wehnelt cylinder placed substantially around said ion source.

25. An ion mobility spectrometer according to claim 1, wherein the aperture of the entrance diaphragm of cell A in said decelerating ion gate is equal to $\sigma_0$.

26. An ion mobility spectrometer according to claim 1 wherein the gas or gas mixture in all or only in part of said ion mobility spectrometer is enriched or replaced by another gas.

27. An ion mobility spectrometer according to claim 26 the gas or gas mixture contains at least a few percentage of He or of $CO_2$.

28. A method of executing an ion mobility spectrometer, wherein the ion mobility spectrometer comprises
an ion source for generating ions;
an ion detector for detecting ions, and
a number of substantially flat diaphragm electrodes arranged substantially perpendicular to a straight system axis that extends in a forward direction from said ion source to said ion detector and that passes through apertures of said diaphragms, the electrodes being arranged in a series of cells with each cell comprising an entrance and an exit diaphragm and a short region in between so that the exit diaphragm of one cell is identical to the entrance diaphragm of the next cell,
wherein said cells of said ion mobility spectrometer are grouped into three regions:
an ion-beam forming region comprising at least one of said cells with its diaphragms having apertures of substantially equal areas $\sigma_0$ and being placed at static potentials that establish electric forward fields $\geq E_H$, where $E_H$ having a magnitude such that ions of mobility $K_0$ would move forward with a velocity $v_H = K_0 E_H$ of about several meters per second;

an ion analyzing region comprising at least one of said cells with its diaphragms having apertures, whose areas are substantially larger than $\sigma_0$, and being placed at static potentials that establish electric forward fields $\geq E_H$; and an ion gate region placed downstream of said ion-beam forming region and upstream of said ion analyzing region wherein said ion gate region comprises at least two cells: an initial cell A of length $l_A$ and a final cell B of length $l_B$, wherein an entrance diaphragm of said cell A has an aperture whose area is substantially equal to the areas of the apertures of the diaphragms in said ion-beam forming region while an exit diaphragm of said cell B has an aperture whose area is substantially equal to the areas of the apertures of the diaphragms in said ion analyzing region while all other diaphragms in said ion gate have apertures whose areas are in between the area of the aperture of the entrance diaphragm of said cell A and the area of the aperture of the exit diaphragm of said cell B;

the method comprising:

selecting the magnitudes of said fields to move the ions of interest of mobilities $K_0$ with velocities $K_0 E_H \geq 10$ m/s in the ion-beam forming region; and selecting the magnitudes of said fields to move the ions of interest of mobilities $K_0$ with velocities $K_0 E_H \geq 10$ m/s in the ion analyzing region.

29. The method according to claim 28, further comprising:

selecting during a first time period $T_1$ the potentials of the entrance and exit diaphragms of said cell A so that along said system axis in said cell A a low electric forward field, $E_{A,L}$, where $E_{A,L} \leq E_H/10$ is established, while along said system axis in a last cell of said ion-beam forming region the electric forward field is $\geq E_H$, causing ions to be pushed out of this cell and into said cell A, where they are slowed down and so form a dense ion bunch; and selecting $T_1$ to be longer than the ions of interest of mobility $K_0$ need to move through the length of said cell A in the low field $E_{A,L}$, where $T_1 \geq l_A/(K_0 E_{A,L})$.

30. A method according to claim 29, further comprising:

selecting during a second time period $T_2$ the potentials of the diaphragms in said cell A and in said cell B so that along said system axis in said cell B a low electric field, $E_{B,L}$, where $E_{B,L} \leq E_H/10$ is established and in cell A a high electric forward field, $E_{A,H}$, where $E_{A,H} \geq E_H$, causing ions to be pushed out of cell A and into cell B, where they are slowed down and form an ion bunch that is shorter and denser than it was in cell A at the beginning of said time period $T_2$; and selecting $T_2$ to be longer than the ions of interest of mobility $K_0$ need to move through the length of said cell A in the high field $E_{A,H}$, where $T_2 \geq l_A/(K_0 E_{A,H})$.

31. A method according to claim 30, further comprising:

selecting a third time period $T_3$ the potentials of the entrance and exit diaphragms in said cell B so that along said system axis in said cell B a high electric field, $E_{B,H}$, where $E_{B,H} \geq E_H$, is established, while the electric forward field along said system axis in the first cell of said ion analyzing region is also $\geq E_H$, so that ions are pushed out of said cell B and into the first cell of the ion analyzing region, with the ion bunch keeping approximately the shape it had at the beginning of said time period $T_3$; and selecting $T_3$ to be longer than the ions of interest of mobility $K_0$ need to move through the length of said cell B in the high field $E_{B,H}$, where $T_3 \geq l_B/(K_0 E_{B,H})$.

* * * * *

UNITED STATES PATENT AND TRADEMARK OFFICE
CERTIFICATE OF CORRECTION

PATENT NO. : 9,508,535 B2
APPLICATION NO. : 14/384039
DATED : November 29, 2016
INVENTOR(S) : Hermann Wollnik and Gary A. Eiceman Page 1 of 1

It is certified that error appears in the above-identified patent and that said Letters Patent is hereby corrected as shown below:

In the Specification

Column 3, Line 2, "$1/[(K_0+\Delta K)E_{A,2}]$" should be --$1_B/[(K_0+\Delta K)E_{B,2}]$--

Column 3, Line 13, "$V_{B,2}=(K_0\pm\Delta K)E_{B,2}$" should be --$V_{B,3}=(K_0-\Delta K)E_{B,3}$--

Column 3, Line 15, "$\geq 1_B/(K_0\pm\Delta K)E_{B,3}$" should be --$\geq 1_B/(K_0-\Delta K)E_{B,3}$--

Column 5, Line 26, "5, 8, and 9" should be --5, 9, and 10--

In the Claims

Column 11, Line 31, "$E_{A,1}\geq E_H/10$" should be --$E_{A,1}\leq E_H/10$--

Column 13, Line 51, "of cell and" should be --of cell A and--

Signed and Sealed this
Twenty-third Day of January, 2018

Joseph Matal
*Performing the Functions and Duties of the
Under Secretary of Commerce for Intellectual Property and
Director of the United States Patent and Trademark Office*